United States Patent
Stengel

(10) Patent No.: US 8,858,585 B2
(45) Date of Patent: Oct. 14, 2014

(54) DEVICE AND METHOD FOR REDUCING OR REMOVING STENOSES

(75) Inventor: Max Stengel, Bruchsal (DE)

(73) Assignee: Variomed AG, Balzers (LI)

( * ) Notice: Subject to any disclaimer, the term of this patent is extended or adjusted under 35 U.S.C. 154(b) by 1357 days.

(21) Appl. No.: 12/377,838

(22) PCT Filed: Aug. 7, 2007

(86) PCT No.: PCT/EP2007/006980
§ 371 (c)(1), (2), (4) Date: Jul. 20, 2010

(87) PCT Pub. No.: WO2008/022710
PCT Pub. Date: Feb. 28, 2008

(65) Prior Publication Data
US 2010/0312262 A1 Dec. 9, 2010

(30) Foreign Application Priority Data
Aug. 21, 2006 (DE) .......................... 10 2006 039 236

(51) Int. Cl.
*A61M 29/00* (2006.01)
*A61M 25/10* (2013.01)
*A61M 25/00* (2006.01)

(52) U.S. Cl.
CPC ... *A61M 25/1018* (2013.01); *A61M 2025/0036* (2013.01); *A61M 25/104* (2013.01); *A61M 2025/1052* (2013.01)
USPC ........... 606/194; 606/159; 606/200; 623/1.11

(58) Field of Classification Search
USPC ............... 604/96.01, 101.04, 101.05, 103.03, 604/103.04, 103.07, 4.01, 101.01, 907, 604/913; 606/194, 198, 200, 159; 623/1.11, 623/1.12, 903, 1.35, 1.27
See application file for complete search history.

(56) References Cited

U.S. PATENT DOCUMENTS 4,651,738 A * 3/1987 Demer et al. .................. 606/194
4,781,192 A * 11/1988 Demer ........................... 606/195
(Continued)

FOREIGN PATENT DOCUMENTS

WO WO 98/47558 A1 10/1998
WO WO 98/57592 A1 12/1998
WO WO 00/76390 A2 12/2000

OTHER PUBLICATIONS

Fanelli, F., et al., "Techniques in cerebral protection," *European Journal of Radiology* 60, pp. 26-36 (2006).
(Continued)

*Primary Examiner* — David Eastwood
(74) *Attorney, Agent, or Firm* — Kilpatrick Townsend & Stockton LLP

(57) ABSTRACT

A device for reducing or removing stenosis present in a blood vessel by means of a working catheter (7) is described. The working catheter comprises a lumen (8) forming a first working channel (9), extending from the distal end (11) to the proximal end of the working catheter for inserting an instrument (38) to reduce or remove the stenosis. Furthermore, a balloon catheter (16) is provided, which is configured separately from the working catheter, the balloon catheter comprising a sealing balloon (22) in the region of the distal end (21) thereof. The balloon catheter comprises two lumen (18, 20) that are configured separately from each other, of which one is connected to the sealing balloon for the dilation of the same, while the other one forms a second working channel (19) extending from the distal end to the proximal end of the balloon catheter. The sealing balloon is configured for the lateral encompassing of the distal end region of the working catheter such that if a working catheter and a balloon catheter are inserted into the blood vessel next to each other a seal is formed between the outsides of the working catheter and of the balloon catheter and the inside wall of the blood vessel by means of the dilated sealing balloon.

22 Claims, 4 Drawing Sheets

(56) References Cited

U.S. PATENT DOCUMENTS

Figure 1:
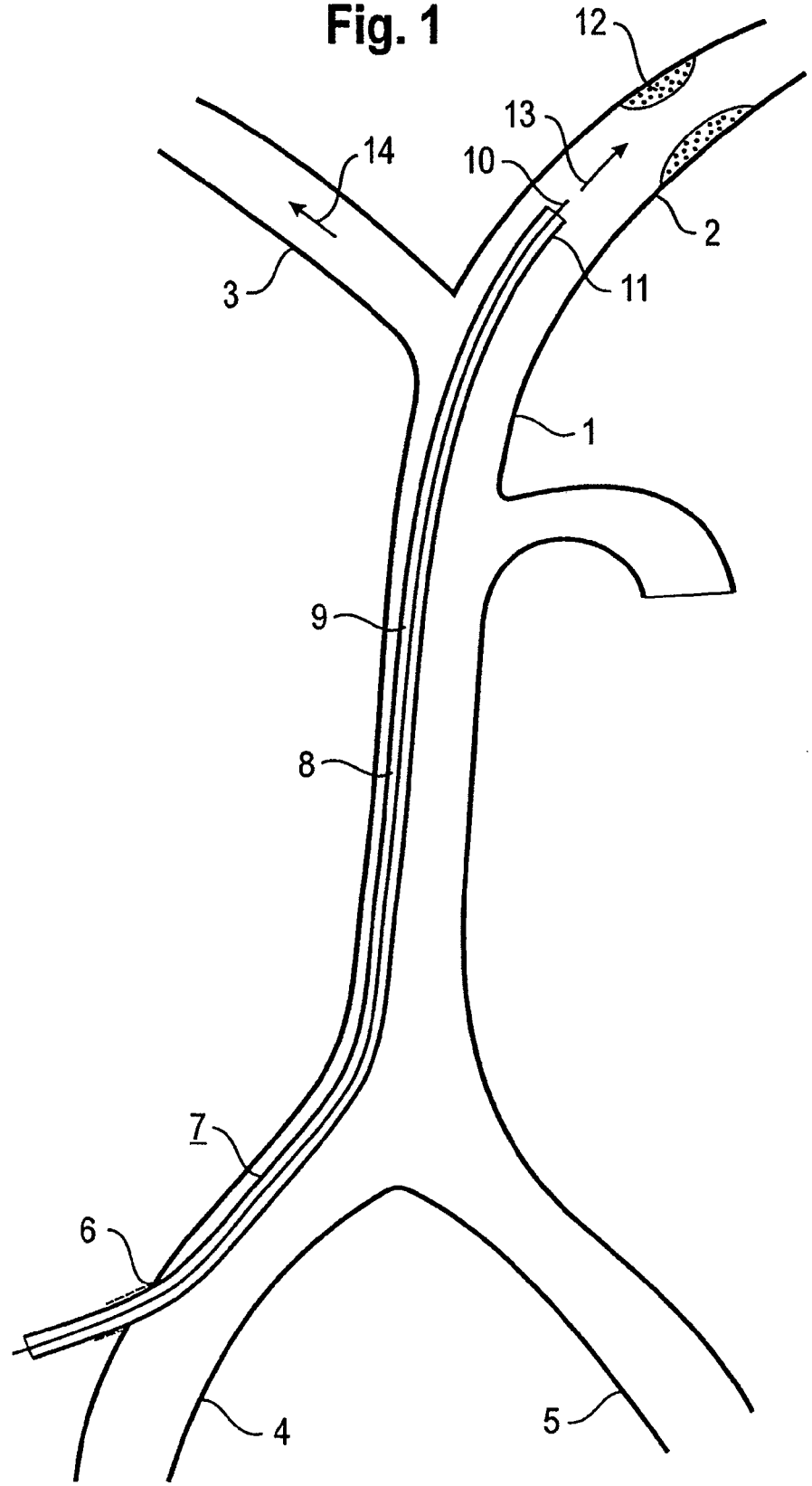

| | | | |
|---|---|---|---|
| 4,983,167 A * | 1/1991 | Sahota | 606/194 |
| 5,049,131 A * | 9/1991 | Deuss | 604/98.01 |
| 5,108,370 A * | 4/1992 | Walinsky | 604/102.02 |
| 5,320,605 A * | 6/1994 | Sahota | 604/101.01 |
| 5,338,300 A * | 8/1994 | Cox | 604/103.05 |
| 5,395,389 A * | 3/1995 | Patel | 606/194 |
| 5,575,771 A * | 11/1996 | Walinsky | 604/96.01 |
| 5,613,946 A * | 3/1997 | McKeever | 604/96.01 |
| 5,800,518 A * | 9/1998 | Piplani et al. | 128/898 |
| 6,007,517 A * | 12/1999 | Anderson | 604/103.04 |
| 6,146,370 A * | 11/2000 | Barbut | 604/500 |
| 6,346,089 B1 * | 2/2002 | Dibie | 623/1.15 |
| 6,673,040 B1 * | 1/2004 | Samson et al. | 604/101.01 |
| 7,374,560 B2 * | 5/2008 | Ressemann et al. | 604/509 |
| 7,740,609 B2 * | 6/2010 | Rowe et al. | 604/101.05 |
| 7,998,104 B2 * | 8/2011 | Chang | 604/9 |
| 2001/0001812 A1 * | 5/2001 | Valley et al. | 604/96.01 |
| 2001/0003795 A1 * | 6/2001 | Suresh et al. | 604/96.01 |
| 2001/0016725 A1 * | 8/2001 | Valley et al. | 604/509 |
| 2001/0044598 A1 | 11/2001 | Parodi | |
| 2001/0047184 A1 * | 11/2001 | Connors, III | 606/194 |
| 2001/0056274 A1 * | 12/2001 | Perkins et al. | 604/516 |
| 2002/0016564 A1 * | 2/2002 | Courtney et al. | 604/96.01 |
| 2002/0185135 A1 * | 12/2002 | Amar | 128/207.15 |
| 2005/0154298 A1 | 7/2005 | Barbut | |
| 2005/0154344 A1 | 7/2005 | Chang | |
| 2005/0228432 A1 | 10/2005 | Hogendijk et al. | |
| 2005/0245866 A1 * | 11/2005 | Azizi | 604/96.01 |
| 2005/0277979 A1 | 12/2005 | Dorros et al. | |

OTHER PUBLICATIONS

Yadav, Jay S., "Embolic Protection Devices: Methods, Techniques, and Data," *Techniques in Vascular and Interventional Radiology 7*, pp. 190-193 (2005).

* cited by examiner

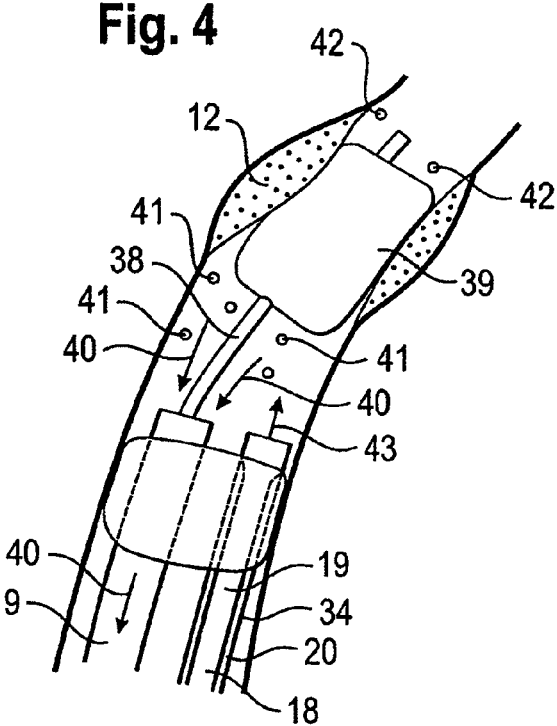
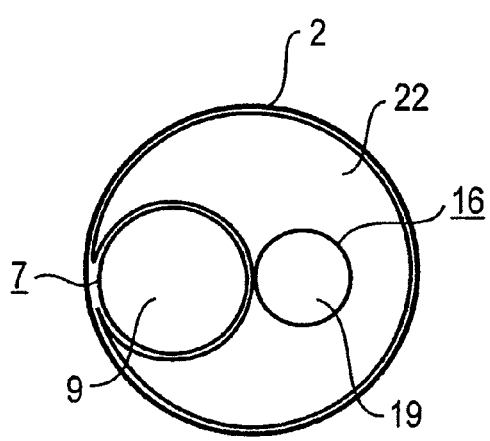
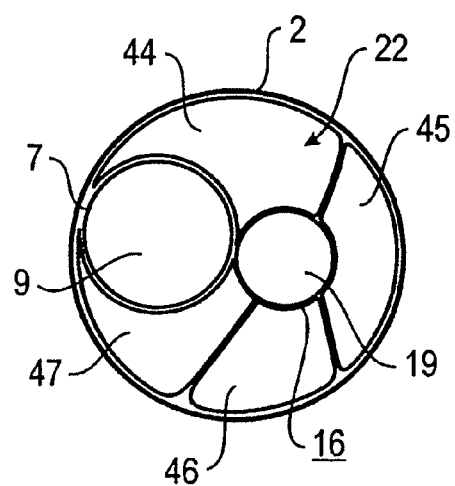

DEVICE AND METHOD FOR REDUCING OR REMOVING STENOSES

CROSS-REFERENCE TO RELATED APPLICATIONS

This application is a National Stage of International Application No. PCT/EP2007/006980 filed Aug. 7,2007 , and which claims benefit of German Patent Application No. 10 2006 039 236.1, filed Aug. 21, 2006, the disclosures of which are incorporated herein by reference.

The present invention relates to a device for the reduction or the removal of a stenosis present in a blood vessel having a working catheter with a lumen which forms a first working channel extending from the distal end up to the proximal end of the working catheter for the introduction of an instrument for the reduction or removal of the stenosis. The invention is furthermore directed to a method for the reduction or the removal of a stenosis present in a blood vessel, wherein a working catheter is introduced via an access into the blood vessel until the distal end of the working catheter comes to lie in the region proximal to the stenosis, with the working catheter having a lumen which forms a first working channel extending from the distal end up to the proximal end of the working catheter.

Devices and methods of this kind are used, for example, for the removal of stenoses in the arteria carotis and in particular in the arteria carotis interna. In this respect, the expansion of the stenosis can, for example, take place by balloon dilatation, with a stent additionally being able to be deposited in the region of the stenosis to ensure the expanded state in the long term. It is furthermore also possible to remove and suck off at least some of the deposits.

It is generally problematic that both on balloon dilatation and in the positioning of the stent or on the mechanical processing of the stenosis deposits can be released which can move toward the brain due to the antegrade flow in the aorta carotis interna and can trigger a stroke there. This must be therefore be avoided under all circumstances.

Known devices and methods therefore frequently use a so-called protection system by which the arteria carotis interna is blocked distal of the stenosis so that particles being released on the treatment of stenosis cannot be transported in the direction of the brain. It is, however, problematic with these devices that before the protection system becomes effective it must first be guided through the stenosis to be able to become active in the region distal of the stenosis. When guiding through the stenosis, however, there is a danger that parts of the stenosis will already be released and migrate in the direction of the brain.

Devices are therefore already known in which a guide wire is guided via the working channel of the working catheter and a protection element, for example in the form of a balloon, is provided at its distal end. This protection element is introduced via the working channel of the catheter into the arteria carotis externa to stop the blood flow there and to achieve a flow reversal in the arteria carotis interna after connecting the proximal end of the working channel to a vein. For this purpose, the working catheter has a balloon at its distal end with which the arteria carotis communis is blocked so that a backflow is produced which takes place from the arteria carotis interna through the working channel of the working catheter.

It is problematic with this device that the puncture channel usually applied in the region of the thigh or of the groin for the introduction of the working catheter has to be made relatively large since the working catheter has a relatively large diameter. This is due to the fact that the working catheter has to include both the blocking element for the blocking of the arteria carotis communis and a working channel through which both the blocking element for the blocking of the arteria carotis externa and the instrument for the removal of the stenosis have to be guided, with simultaneously a sufficient retrograde blood flow through the working channel having to be ensured. Furthermore, an outer cover (sluice) is usually provided at the outer side of the working catheter by which the outwardly disposed balloon is covered on the introduction of the working catheter. The diameter of the working catheter is further enlarged by this sluice.

It is problematic with these large puncture points that their healing often only takes place relatively poorly and the risk of inflammation is thereby also increased. The problem furthermore exists on the use of a single working channel that the working channel is often completely occupied by the instruments guided through the working channel so that a sufficient retrograde blood flow through the working channel is not ensured in all cases.

It is an object of the present invention to develop a device and a method of the initially named kind such that the named disadvantages are avoided.

Starting from a device of the initially named kind, this object is satisfied in that a balloon catheter is provided which is made separate from the working catheter and which includes a sealing balloon in the region of its distal end; in that the balloon catheter includes two lumens which are made separate from one another and of which one is connected to the sealing balloon for the dilatation thereof, whereas the other forms a second working channel extending from the distal end up to the proximal end of the balloon catheter; and in that the sealing balloon is made to engage laterally around the distal end region of the working catheter so that, when the working catheter and the balloon catheter are introduced next to one another into the blood vessel, a seal is formed by the dilatated sealing balloon between the outer sides of the working catheter and of the balloon catheter as well as the inner wall of the blood vessel.

The part of the object relating to the method is satisfied starting from a method of the initially named kind in that a balloon catheter made separate from the working catheter is introduced into the blood vessel via a second access separate from the first access until the distal end of the balloon catheter comes to lie in the region next to the distal end of the working catheter, with the balloon catheter including in the region of its distal end a sealing balloon as well as two lumens which are made separate from one another, of which one is connected to the sealing balloon for the dilatation thereof, whereas the other forms a second working channel extending from the distal end up to the proximal end of the balloon catheter; in that the sealing balloon is dilatated via the lumen so that the distal end region of the working catheter is engaged around by the sealing balloon so that a seal is formed between the outer sides of the working catheter and of the balloon catheter as well as the inner wall of the blood vessel; and in that an instrument for the reduction or the removal of the stenosis is introduced into the blood vessel via the first working channel.

In accordance with the invention, a division into two mutually separate catheters thus takes place, namely into a working catheter and a balloon catheter which are introduced into the blood vessel via two separate accesses. Due to the division into two separate catheters, the two required accesses can each be made considerably smaller than is the case with a common catheter. Problems in the healing of the corresponding puncture positions are thereby reliably avoided. It is generally possible in this respect to lay one respective access per leg or to provide both accesses ipsilaterally, but separate from one another.

It is furthermore achieved by the division into two working channels that a constant retrograde blood flow can be maintained through the first working channel by which it is ensured that particles released on the dilatation of the stenosis do not migrate toward the brain, but are sucked off reliably, whereas simultaneously a weaker antegrade blood flow can be maintained through the second working channel. The administration of contrast media, medication, or NaCl is therefore possible through the second working channel without any risk of carrying along an embolism.

Since no outwardly disposed balloon is provided at the working catheter, no outwardly disposed sluice is required at the working catheter so that accordingly the first working channel can be formed with an enlarged lumen, which facilitates the handling capability on balloon dilatation, for example, as well as on the insertion of a stent and simultaneously ensures that a constant backflow is maintained through the first working channel. Even if the first working channel is briefly blocked on the introduction of a stent or of a balloon, a pressure build-up in the arteria carotis interna is avoided by the second working channel. A corresponding pressure build-up is also avoided in the arteria carotis externa since a blocking of the arteria carotis externa is superfluous.

It is ensured by the specific formation of the sealing balloon to engage laterally around the distal end region of the working catheter that the backflow built up by the first working channel is reliably maintained so that any particles released during the treatment of the stenosis are led off together with the backflow through the first working channel. Due to the specific formation of the sealing balloon only one single balloon is required for the sealing of the arteria carotis interna even though two separate catheter systems are used. The arteria carotis externa is likewise separated from the stenosis in this manner, but without a blocking of the arteria carotis externa being necessary.

In accordance with an advantageous embodiment of the invention, the sealing balloon has an asymmetrical cross-section. The sealing engaging around of the working catheter by the sealing balloon can be further improved by the use of an asymmetric cross-section.

In accordance with a further preferred embodiment of the invention, the sealing balloon includes a plurality of individual balloons. The engaging around of the working catheter can be improved by this division of the sealing balloon and an automatic alignment of the balloon catheter to the working catheter can be achieved.

A venous sluice is advantageously provided via which the first working channel can be connected to a vein. It is achieved by the different pressure relationships in the vein and the artery that a constant backflow through the first working channel is maintained which reliably transports away released particles of the stenosis. It is, however, generally also possible that the backflow through the working channel is not led off into a vein, but to the exterior, for example.

In accordance with a further preferred embodiment of the invention, the first and/or the second working channel(s) is/are made for the reception of a guide wire. Both the working catheter and the balloon catheter can thus be introduced via an initially laid guide wire to the desired position proximal to the stenosis. After the positioning has taken place, the guide wire is removed in the usual fashion so that the first and/or the second working channel(s) is/are available for further use.

The second working channel is preferably made for the injection of liquid, in particular of contrast media, of medication or of NaCl. For this purpose, a lateral connection is, for example, provided at the second working channel in the region of its proximal end. Although a constant backflow through the first working channel is present in the retrograde direction which ensures a reliable leading away of any released particles of the stenosis, an antegrade flow can simultaneously be provided through the second working channel via which an injection is possible in the direction of the stenosis.

In accordance with a further preferred embodiment, a pressure generating unit is provided for the generation of a constant pressure, said pressure generating unit being connected to the sealing balloon via the lumen of the balloon catheter connected to the sealing balloon and with the pressure within the sealing balloon being kept substantially constant by said pressure generating unit after the dilatation of the sealing balloon. It is ensured by the pressure generating unit that the seal between the catheters and the inner housing wall is also ensured on a drop of the pressure in the sealing balloon, for example due to a leak.

The pressure generating unit can, for example, preferably include a pressure compensation tank whose lumen is in particular substantially larger than the lumen of the sealing balloon. Since the sealing balloon usually has a very small volume, an almost constant pressure can be maintained in the sealing balloon in a simple manner by a correspondingly large compensation tank. Slight pressure fluctuations in the sealing balloon can easily be compensated by the large volume of the pressure compensation tank.

In accordance with a further advantageous embodiment of the invention, the first working channel has a larger diameter than the second working channel. Since both the instrument for the removal of the stenosis is guided through the first working channel and simultaneously a sufficient cross-section should be available for the backflow, whereas only the optional supply of contrast medium or the like is carried out through the second working channel, it is advantageous if the first working channel has a larger diameter than the second working channel. It is furthermore thereby ensured that the desired flow removal is maintained in all cases in the arteria carotis interna.

In accordance with a further preferred embodiment of the invention, the working catheter has a diameter of approximately 5 to 9 French, in particular of approximately 6 to 8 French, preferably of approximately 7 French. The balloon catheter can preferably have a diameter of 10 to 14 mm, in particular of approximately 12 mm. The diameter of the puncture channel can in particular be minimized for the working catheter, whereby the healing conditions for the puncture point are considerably improved.

The sealing balloon preferably has an axial length of approximately 0.5 to 3 cm, in particular of approximately 1 to 1.5 cm. These lengths of the sealing balloon are usually sufficient to ensure an ideal compromise between seal and space requirements.

In accordance with a further preferred embodiment of the invention, the sealing balloon comprises elastic material. It is generally also possible that the sealing balloon comprises inelastic material or semi-elastic material. It is important that the sealing balloon is selected with respect to its material and its other properties, for example its material thickness, such that an enclosing of the working catheter which is as complete as possible takes place on the balloon dilatation and such that the balloon material in particular also fills up all the gaps present between the working catheter and the inner vessel wall so that the seal is as complete as possible.

For this purpose, for example, the maximum diameter of the sealing balloon can preferably be larger than the diameter of the blood vessel. This has the result that, with a not yet completely dilatated balloon, the balloon skin is not stressed and can thus more easily fit snugly to the outer contour of the working catheter and to the inner side of the vessel and can in particular also slip into small gaps between the working catheter and the inner housing wall.

Further preferred embodiments are set forth in the dependent claims.

Figure 2:
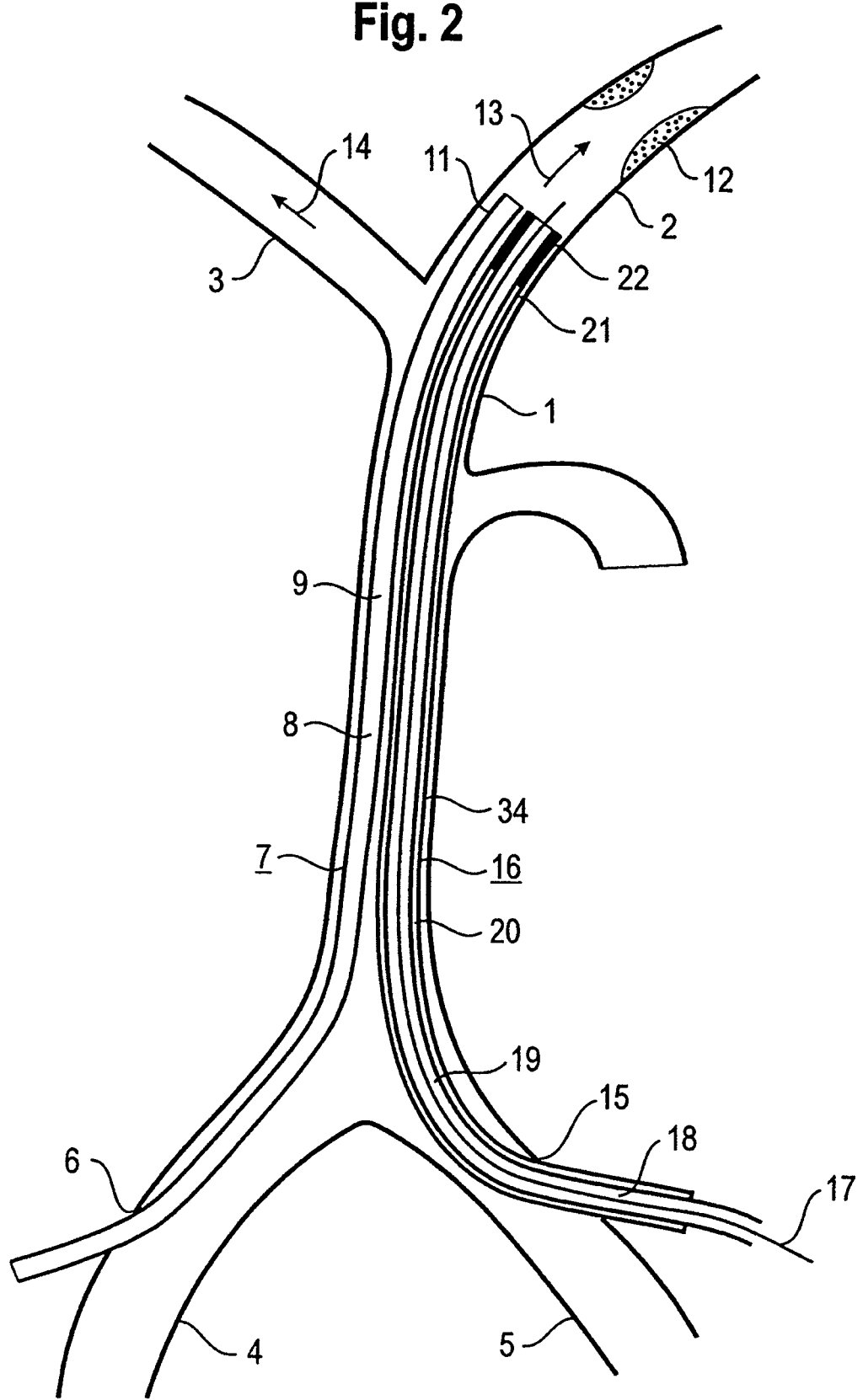
Figure 3:
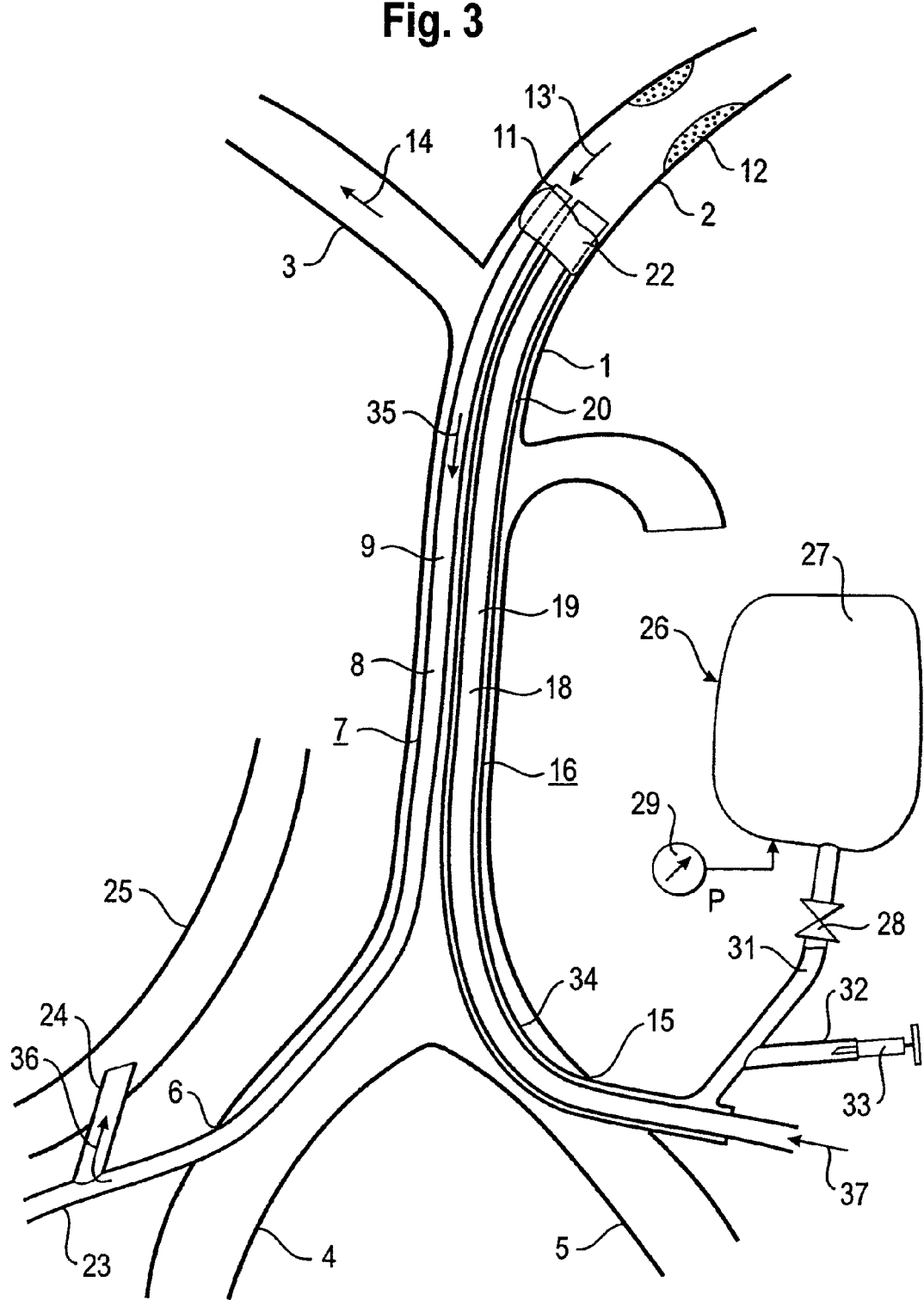

The invention will be described in more detail in the following with reference to embodiments and to the drawings; there are shown in these:

FIG. 1 a very simplified representation of a working catheter which is introduced into the arteria carotis interna through the arteria femoralis;

FIG. 2 the representation in accordance with FIG. 1 with an additionally introduced balloon catheter;

FIG. 3 a device made in accordance with the invention with a working catheter and a balloon catheter in the completely introduced state;

FIG. 4 a detailed view of a device made in accordance with the invention;

FIG. 5 a schematic cross-section through the arteria carotis interna with a device made in accordance with the invention in accordance with a first embodiment; and FIG. 6 a view in accordance with FIG. 5 with a device made in accordance with the invention in accordance with a second embodiment.

FIG. 1 shows in a very simplified representation the arteria carotis communis 1 which branches off into the arteria carotis interna 2 and the arteria carotis externa 3, on the one hand, and is in communication with the two branches 4, 5 of the arteria femoralis, on the other hand.

An access 6 for a working catheter 7 into the branch 4 of the arteria femoralis is provided via a schematically represented puncture channel and extends from the access 6 up to the arteria carotis interna 2. The working catheter 7 includes a lumen 8 which forms a first working channel 9 of the working catheter 7. A guide wire 10 via which the working catheter 7 was introduced into its position shown in FIG. 1 is arranged in the first working channel 9.

A stenosis 12 is present in the arteria carotis interna 2 distal to the distal end 11 of the working catheter 7. The usually present antegrade flow of the blood in the arteria carotis interna 2 as well as in the arteria carotis externa 3 is furthermore indicated by arrows 13, 14.

The use of a device in accordance with the invention will now be described in more detail with reference to FIG. 1 and to the further Figures.

The working catheter 7 is first introduced in the usual manner via the laid guide wire 10 starting from the access 6 via the branch 4 of the arteria femoralis until its distal end 11 comes to lie proximal from the stenosis 12, as is shown in FIG. 1. Since the working catheter 7 is only a simple catheter with an inwardly disposed first working channel 9, a vessel sluice 6 to 7 French or a guide catheter 7 to 8 French can, for example, be used for the access 6.

After positioning has taken place, the guide wire 10 can be removed. The stenosis 12 is not affected by the introduction of the working catheter 11 so that there no risk of an embolism.

Subsequently, a balloon catheter 16 is introduced in the branch 5 of the arteria femoralis via a second access 15 (FIG. 2) and is advanced parallel to the working catheter 7 up to and into the arteria carotis interna 2. The introduction of the balloon catheter 16 in turn takes place in the usual fashion in this respect via a guide wire 17. Since the working catheter 7 was already previously laid, this second sounding is without problem.

The balloon catheter 16 includes an inwardly disposed lumen 18 by which a second working channel 19 is formed and in which the guide wire 17 is arranged on the introduction of the balloon catheter 16.

The balloon catheter 16 furthermore includes an outwardly disposed lumen 20 which is in communication with a sealing balloon 22 arranged at the distal end 21 of the balloon catheter 16. An outer cover (sluice) 34 which is connected to the sealing balloon 22 is provided at the outer side of the balloon catheter 16 to form the lumen 20.

As is indicated in FIG. 3, the proximal end 23 of the first working channel 9 is connected via a shunt 24 to a vein 25, for example to the vena femoralis.

A pressure generating unit 26 is furthermore shown in FIG. 3 which includes a pressure compensation tank 27 which is connected via a valve 28 to the lumen 20 of the balloon catheter 16. A display unit 29 (manometer) is furthermore connected to the pressure compensation tank 27 to display the pressure present in the pressure compensation tank 27. The pressure compensation tank 27 is filled with NaCl, for example. A pressure generator can furthermore be connected to the pressure compensation tank 27 via which a desired pressure can be generated and kept constant. The desired pressure can, however, also be generated by a single filling of the pressure compensation container 27.

The pressure generating unit 26 is connected to the lumen 20 of the balloon catheter 16 via a Y connection 30 at whose one branch 31 the pressure generating unit 26 is provided and a connection for a syringe 33 is provided at the other branch 32. NaCl can, for example be supplied via the syringe 33 via the lumen 20 to the sealing balloon 22 of the balloon catheter 16 so that it expands and adopts its completely dilatated shape shown in FIG. 3. After the complete dilatation of the sealing balloon 22, the pressure is maintained therein by the pressure generating unit 26.

The sealing balloon 22 expands by the dilatation thereof so that it engages around the distal end 11 of the working catheter 7, as can in particular be recognized from FIGS. 5 and 6. The sealing balloon 22 in this respect expands such that it contacts the inner wall of the arteria carotis interna 2 as well as the outer side of the working catheter 7, on the one hand, and also enters largely completely into the constricted points between the inner wall of the arteria carotis interna 2 and the working catheter 7, on the other hand. A complete blocking of the arteria carotis interna 2 is achieved in this manner by the sealing balloon 22.

A flow reversal which is indicated by arrows 13', 35 and 36 in FIG. 3 takes place in the arteria carotis interna 2 by this blocking and the connection of the first working channel 9 to the vein 25. Despite this flow reversal, it is possible to introduce contrast media, medication or NaCl, for example, into the arteria carotis interna 2 via the second working channel 19 of the balloon catheter 16 in the antegrade direction in accordance with an arrow 37. The normal flow in the arteria carotis externa 3 in accordance with the arrow 14 is not influenced by the blocking of the arteria carotis interna 2.

Once the blocking system in accordance with the invention has been completely positioned in accordance with FIG. 3, an instrument for the reduction or the removal of the stenosis 12 can be introduced through the first working channel. This can be made, for example, as a further catheter 38 with a dilatation balloon 39 at its distal end, as is indicated in FIG. 4. The stenosis 12 can be expanded in the usual manner via the dilatation balloon 39. It is also possible that a stent is introduced into and is positioned in the region of the stenosis 12 in a known manner as well as expanded via the dilatation balloon 39. On the introduction of a self-expanding stent, the expansion via the dilatation balloon 39 can also be dispensed with.

Despite the introduced catheter 38, the backflow through the first working channel 9 is maintained for as long as the flow through the completely expanded dilatation balloon 39 is not interrupted, as is indicated by arrows 40 in FIG. 4. If deposits 41 should be released on the expansion of the stenosis 12, they are sucked into the first working channel 9 due to the backflow in the arrow direction 40 and thus do not result in an embolism. Deposits 42 possibly released distally of the dilatation balloon 39 are also sucked off after the folding together of the dilatation balloon 39 and the backflow via the first working channel 9 of the working catheter 7 which is thereupon adopted. This also applies if contrast medium is, for example, injected via the second working channel 19 in the antegrade direction in accordance with an arrow 43 since the flow can be set overall via the larger diameter of the first working channel 9, on the one and, and via the control of the flow in the antegrade direction through the second working channel 19, on the other hand, so that there is a main flow in the retrograde direction.

Whereas in the embodiment in accordance with FIG. 5, the sealing balloon 22 is made as a one-part balloon so that it surrounds the working catheter 7 to seal the arteria carotis interna 2, an embodiment is shown in FIG. 6 in which the sealing balloon 22 consists of four part balloons 44 to 47. In the embodiment shown in FIG. 6, no alignment of the balloon catheter 16 to the working catheter 7 is thus required to reliably achieve an engaging around of the working catheter 7 and thus a seal of the arteria carotis interna 2.

Whereas in the embodiments shown in the Figures the device in accordance with the invention was in each case described for the treatment of a stenosis in the arteria carotis interna, the invention can generally also be used for stenoses in other blood vessels. The embodiments should therefore not represent any restrictive effect for the use specifically in the arteria carotis interna.

REFERENCE NUMERAL LIST 1 arteria carotis communis
2 arteria carotis interna
3 arteria carotis externa
4 branch of the arteria femoralis
5 branch of the arteria femoralis
6 access
7 working catheter
8 lumen
9 first working channel
10 guide wire
11 distal end of the working channel
12 stenosis
13, 13' arrow
14 arrow
15 access
16 balloon catheter
17 guide wire
18 lumen
19 second working channel
20 lumen
21 distal end of the balloon catheter
22 sealing balloon
23 proximal end of the working channel
24 shunt
25 vein
26 pressure generating unit
27 pressure compensation tank
28 valve
29 display
30 Y connection
31 branch of the Y connection
32 branch of the Y connection
33 syringe
34 sluice
35 arrow
36 arrow
37 arrow
38 catheter
39 dilatation balloon
40 arrow
41 deposit
42 deposit
43 arrow
44 part balloon
45 part balloon
46 part balloon
47 part balloon

The invention claimed is:

1. A device for the reduction or the removal of a stenosis present in a blood vessel, comprising:
    a working catheter with a lumen which defines a first working channel extending from a distal end up to a proximal end of the working catheter for the introduction of an instrument for the reduction or the removal of the stenosis; and
    a balloon catheter which is separate from the working catheter, comprising:
        a sealing balloon in the region of a distal end of the balloon catheter;
        a first lumen connected to the sealing balloon for the dilation of the sealing balloon; and
        a second, separate lumen which defines a second working channel extending from the distal end of the balloon catheter up to a proximal end of the balloon catheter,
    wherein the sealing balloon, when dilated, comprises an asymmetrical cross-section configured to engage laterally around a distal end region of the working catheter so that, when the working catheter and the balloon catheter are introduced next to one another into the blood vessel, a seal is formed by the dilated sealing balloon between outer sides of the working catheter, the balloon catheter and an inner wall of the blood vessel.

2. A device in accordance with claim 1, wherein the sealing balloon comprises a plurality of individual balloons.

3. A device in accordance with claim 1, further comprising a venous sluice via which the first working channel can be connected to a vein.

4. A device in accordance with claim 1, wherein at least one of the first or the second working channel is configured to receive a guide wire.

5. A device in accordance with claim 1, wherein the second working channel is configured for a liquid to be injected thereto.

6. A device in accordance with claim 1, further comprising a pressure generating unit configured for generation of a constant pressure, wherein the pressure generating unit is connected via the first lumen of the balloon catheter to the sealing balloon and wherein the pressure generating unit is configured to keep pressure within the sealing balloon substantially constant after dilation of the sealing balloon.

7. A device in accordance with claim 6, wherein the pressure generating unit comprises a pressure compensation tank.

8. A device in accordance with claim 7, wherein the pressure compensation tank has a substantially higher volume than the sealing balloon.

9. A device in accordance with claim 1, wherein the first working channel has a larger diameter than the second working channel.

10. A device in accordance with claim 1, wherein the working catheter has a diameter of approximately 5-9 French.

11. A device in accordance with claim 1, wherein the balloon catheter has a diameter of approximately 7-14 mm.

12. A device in accordance with claim 1, wherein the sealing balloon has an axial length of approximately 0.5-3 cm.

13. A device in accordance with claim 1, wherein the sealing balloon comprises an elastic material.

14. A device in accordance with claim 1, wherein the sealing balloon comprises an inelastic material.

15. A device in accordance with claim 1, wherein a maximum diameter of the sealing balloon is larger than a diameter of the blood vessel.

16. A method for the reduction or the removal of a stenosis present in a blood vessel, comprising:
   introducing a working catheter via a first access into the blood vessel until a distal end of the working catheter comes to lie proximal to the stenosis, wherein the working catheter comprises a lumen which defines a first working channel extending from a distal end up to a proximal end of the working catheter;
   introducing a balloon catheter, separate from the working catheter, into the blood vessel via a second access separate from the first access until a distal end of the balloon catheter comes to lie next to the distal end of the working catheter, wherein the balloon catheter comprises:
      a sealing balloon with an asymmetrical cross-section, near the distal end of the balloon catheter;
      a first lumen connected to the sealing balloon for dilation thereof; and
      a second lumen which defines a second working channel extending from the distal end up to a proximal end of the balloon catheter;
   dilating the sealing balloon via the first lumen so that the distal end of the working catheter is engaged by the sealing balloon so that a seal is formed between outer sides of the working catheter, the balloon catheter and an inner wall of the blood vessel; and
   introducing an instrument for the reduction or the removal of the stenosis into the blood vessel via the first working channel.

17. A method in accordance with claim 16, wherein introducing at least one of the working catheter or the balloon catheter comprises introducing the respective catheter into the blood vessel via a guide wire.

18. A method in accordance with claim 16, wherein the blood vessel is an artery, and wherein the first working channel is connected to a vein so that a reversal of blood flow is generated via the first working channel in a part of the artery disposed distal the sealing balloon.

19. A device in accordance with claim 1, wherein the working catheter has a diameter of approximately 6-8 French.

20. A device in accordance with claim 1, wherein the working catheter has a diameter of approximately 7 French.

21. A device in accordance with claim 1, wherein the balloon catheter has a diameter of approximately 12 mm.

22. A device in accordance with claim 1, wherein the sealing balloon has an axial length of approximately 1-1.5 cm.

* * * * *